(12) United States Patent
Grebner et al.

(10) Patent No.: US 7,591,589 B2
(45) Date of Patent: Sep. 22, 2009

(54) MEDICAL SYSTEM HAVING A C-ARM

(75) Inventors: Albert Grebner, Eckental (DE); Winfried Lurz, Fürth (DE); Stefan Sattler, Forchheim (DE); Manfred Schönborn, Gerhardshofen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/151,609

(22) Filed: May 8, 2008

(65) Prior Publication Data

US 2008/0279340 A1 Nov. 13, 2008

(30) Foreign Application Priority Data

May 9, 2007 (DE) .................. 10 2007 021 770

(51) Int. Cl.
*H05G 1/02* (2006.01)
(52) U.S. Cl. .................. 378/197; 378/196
(58) Field of Classification Search .......... 378/193, 378/196, 197, 62
See application file for complete search history.

(56) References Cited

U.S. PATENT DOCUMENTS

| 6,582,121 B2* | 6/2003 | Crain et al. ............. 378/197 |
| 6,789,941 B1 | 9/2004 | Grady |
| 2003/0112926 A1* | 6/2003 | Atzinger ................ 378/196 |
| 2008/0013690 A1* | 1/2008 | Lurz et al. .............. 378/167 |

FOREIGN PATENT DOCUMENTS

DE 199 58 864 A1 6/2001

* cited by examiner

*Primary Examiner*—Hoon Song

(57) ABSTRACT

The present intervention relates to a medical diagnosis or intervention system with a radiation source, a radiation detector, and a C-arm as a component carrier, to which the radiation source and the radiation detector are fastened. The distance between the radiation source and the radiation detector can be changed by means of a linear guide. The C-arm is fastened to an articulated arm of a robot and the linear guide is arranged in the vicinity of the fastening point of the C-arm on the articulated arm.

13 Claims, 1 Drawing Sheet

MEDICAL SYSTEM HAVING A C-ARM

CROSS REFERENCE TO RELATED APPLICATIONS

This application claims priority of German application No. 10 2007 021 770.8 filed May 9, 2007, which is incorporated by reference herein in its entirety.

FIELD OF THE INVENTION

The present invention relates to a medical diagnosis and/or intervention system as claimed in the claims.

BACKGROUND OF THE INVENTION

With present-day medical diagnosis and intervention systems, which use a so-called C-arm as a component carrier for the imaging components comprising x-ray generation and adjustment (faceplate and x-ray tube) as well as an x-ray image recording device (e.g. a flat screen detector), the distance between the tube generating radiation and the image converter and/or detector can for the most part be adjusted in order to be able to bring the detector as close as possible to the patient to be examined in order to optimize image quality and/or scattered radiation behavior.

FIG. 1 shows a conventional medical diagnosis and/or intervention system. A radiation source 1 and a detector 2 are attached opposite one another to the free ends of a so-called C-arm.

The radiation source 1 is provided with a faceplate 7 and the detector 2 is fastened to the upper free end of the C-arm by way of a linear guide. Arrow 8 indicates the displacement direction of the linear guide. It is thus apparent that the distance 10 between the radiation source 1 and the detector 2 (SID, Source-Image-Distance) can thus be changed. The detector 2 can be moved as close as possible to a patient lying on the couch 4. FIG. 1 shows a position, in which the detector is disposed vertically above the radiation source 1. Certain examinations require the relative orientation of the patient in respect of the radiation source detector axis to be changed. This takes place inter alia by an orbital movement 9 of the C-arm. This is (not shown here) moveably mounted such that the radiation source detector axis is pivoted about a point which corresponds to the center point of the circle on which the C-arm in the shape of a segment of a circle is disposed. The arrangement of the linear guide 5 between the upper free end of the C-arm and the detector 2 is also cumbersome in an area where collisions with other medical devices in the vicinity of the patient to be examined can easily occur and/or where improved patient accessibility is desirable.

SUMMARY OF THE INVENTION

The object underlying the present invention is to present a medical diagnosis and/or intervention system, which simplifies and scales down the mechanical design of the system adjacent to the detector and in which load torques of the system are reduced.

This object is achieved with the features of the claims.

Features of preferred embodiments of the present invention are characterized in the dependent claims.

The present invention is based on the idea that a change in position of a C-arm by means of a robot with an articulated arm is more effective than an orbital drive of a C-arm in the shape of a segment of a circle. The C-arm can thus be scaled down and load torques reduced, as a result of which the dynamics of the system can be improved, thereby enabling new applications and reducing movement artifacts.

BRIEF DESCRIPTION OF THE DRAWINGS

The invention is described in more detail below with reference to the description of an exemplary embodiment in respect of the drawings, in which.

DETAILED DESCRIPTION OF THE INVENTION

Figure 1:
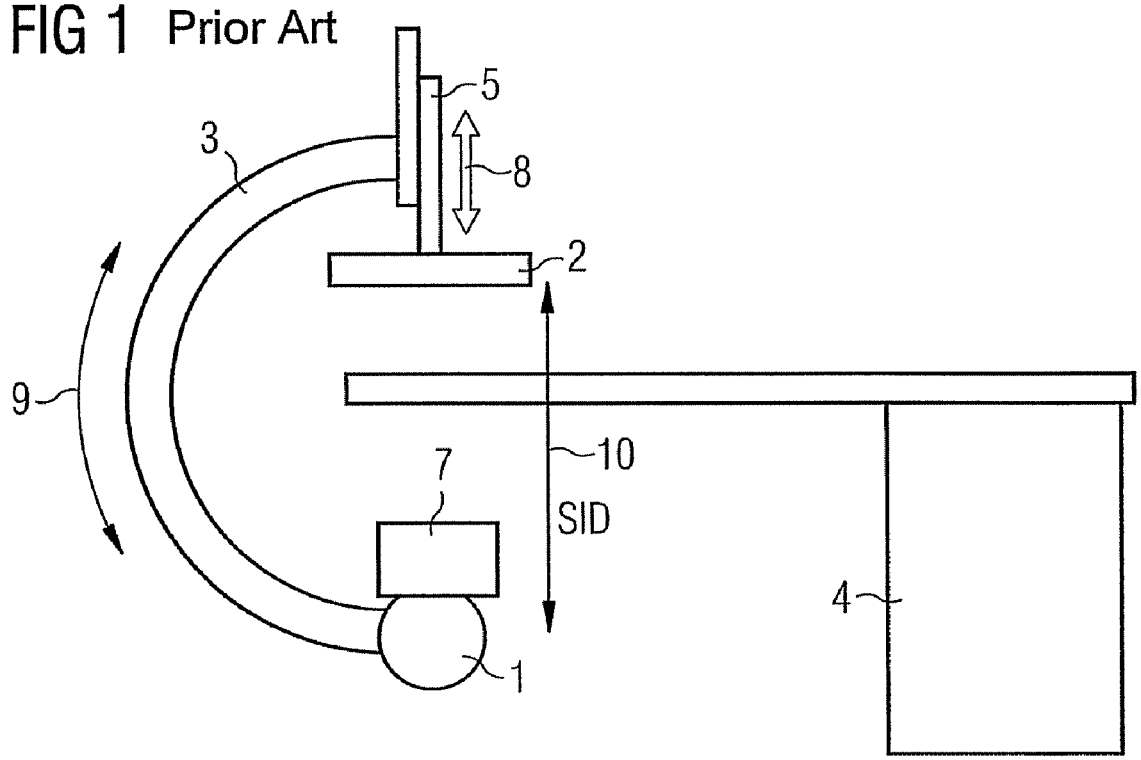
FIG. 1 shows a schematic side view of a conventional medical diagnosis and/or intervention system.
Figure 2:
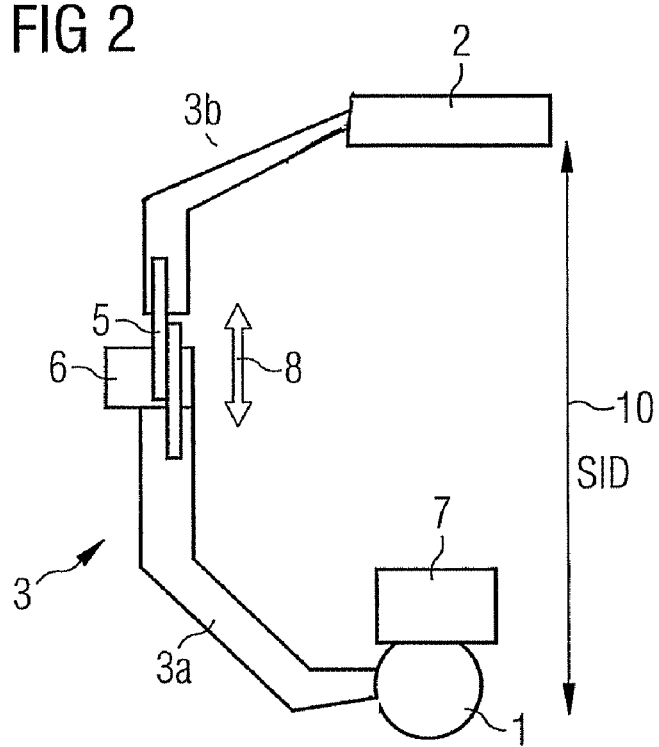
FIG. 2 shows a schematic side view of an exemplary embodiment of an inventive medical diagnosis and/or intervention system.

The design of the system according to the invention essentially differs from a conventional system, as shown in FIG. 1, in that the C-arm is fastened to a free end of an articulated arm (not shown) of a robot by way of a fastening flange 6, and can be moved in three dimensions as a result. This dispenses with the need for the C-arm to be in the shape of a segment of a circle and also allows the linear guide 5 to be repositioned at another location. As shown in FIG. 2, the C-arm 3 of the inventive system consists of a first (lower) part 3a and a second (upper) part 3b. The two parts 3a, 3b of the C-arm 3 are connected with one another by way of a linear guide 5. This is arranged adjacent to the flange point 6 and allows the movement of the upper part 3b specified with the arrow 8. The radiation source detector distance 10 can thus be adjusted. As the linear guide is no longer arranged between the upper free end of the C-arm and the detector, the C-arm can be embodied smaller in comparison with a conventional C-arm shown in FIG. 1. The C-arm no longer necessarily needs to be in the shape of a segment of a circle. This allows parts 3a, 3b of the C-arm to be configured such that they taper at their free ends, which in turn results in a reduction in the load torque, which benefits the dynamics of the system. The top free end of the C-arm part 3b is solely equipped with the detector 2, which noticeably reduces the collision risk with other medical devices or suchlike. The accessibility of the patient to be examined is also improved at this location. The articulated arm robot also enables the detector to be moved into more positions.

The aforementioned description of an exemplary embodiment of the present invention is not to be understood as restrictive, but is used only for illustrative purposes.

The invention claimed is:

1. A medical system, comprising:
    an adjustable C-arm fastened on a flange, the C-arm comprising a rigid first part and a rigid second part, wherein the first part and the second part viewed together substantially form a C-shape;
    a radiation source fastened on the C-arm;
    a radiation detector fastened on the C-arm; and
    a linear guide arranged in the flange for changing a distance between the radiation source and the radiation detector, wherein a change in the distance between the radiation source and the radiation detector is proportional to a linear displacement of the linear guide, and wherein the radiation source and the radiation detector share a common axis of travel.

2. The medical system as claimed in claim 1, wherein the first part comprises the flange and the radiation source.

3. The medical system as claimed in claim 2, wherein the second part comprises the radiation detector and is moved by the linear guide.

4. The medical system as claimed in claim 3, wherein the first part comprises sequentially connected segments that do not share a common longitudinal axis and the second part comprises sequentially connected segments that do not share a common longitudinal axis.

5. The medical system as claimed in claim 4, wherein respective sequentially connected segments are connected in a permanently fixed orientation with respect to adjacent segments.

6. The medical system as claimed in claim 1, wherein the first part tapers at a free end of the first part for reducing a load torque.

7. The medical system as claimed in claim 1, wherein the second part tapers at a free end of the second part for reducing a load torque.

8. The medical system as claimed in claim 1, wherein the first part is arranged beneath the second part.

9. The medical system as claimed in claim 1, wherein the radiation source is an x-ray tube and the radiation detector is a flat screen detector.

10. The medical system as claimed in claim 1, wherein the medical system is a medical diagnosis system or a medical intervention system.

11. A method for assembling a medical system having an adjustable C-arm, wherein the C-arm comprises a first part and a second part, and wherein when the first part and the second part are viewed together they substantially form the shape of a "C", comprising:
 fastening a radiation source of the medical system on the C-arm;
 fastening a radiation detector of the medical system on the C-arm;
 fastening the C-arm on a flange; and
 arranging a linear guide in the flange for changing a distance between the radiation source and the radiation detector, wherein a change in the distance between the radiation source and the radiation detector is proportional to a linear displacement of the linear guide, and wherein the radiation source and the radiation detector share a common axis of travel.

12. The method of claim 11, further comprising constructing the first part with sequentially connected segments that do not share a common longitudinal axis, and constructing the second part with sequentially connected segments that do not share a common longitudinal axis.

13. The method of claim 12, further comprising constructing the first part and the second part using segments that are linear.

* * * * *